US00PP08526P

United States Patent [19]

Wilfret

[11] Patent Number: Plant 8,526

[45] Date of Patent: Dec. 28, 1993

[54] CALADIUM CULTIVAR 'FLORIDA SWEETHEART'

[75] Inventor: Gary J. Wilfret, Bradenton, Fla.

[73] Assignee: University of Florida, Gainesville, Fla.

[21] Appl. No.: 920,079

[22] Filed: Jul. 27, 1992

[51] Int. Cl.[5] ..... A01H 5/00

[52] U.S. Cl. ..... Plt./88.1

[58] Field of Search ..... Plt./88.1

[56] References Cited

PUBLICATIONS

Wilfret, G. J. (Oct. 1991) "Florida Sweetheart: A Rose Lance Caladium for Landscape and Containers" Florida Agricultural Experiment Station Institute of Food and Agriculturel Sciences, University of Floria, Gainsville, Circular S-380.

*Primary Examiner*—James R. Feyrer

*Attorney, Agent, or Firm*—Saliwanchik & Saliwanchik

[57] ABSTRACT

Description and specifications of a new and distinct caladium variety which originated from a cross between 'Candidum Junior' and 'Red Frill' are provided. The new caladium variety is distinct from all others by its color, improved leaf shape, and production of large tubers.

1 Drawing Sheet

SUMMARY OF THE INVENTION

The new and distinct variety of caladium, developed and evaluated as S79-206 at the Gulf Coast Research and Education Center in Bradenton Fla., was derived from a selection made in 1979 from a 1977 cross between 'Candidum Junior' and 'Red Frill'. Ancestry of both parents in unknown, although 'Candidum Junior' is believed to be a field mutation of 'Candidum'. The seed parent, the fancy-leaved 'Candidum Junior', was selected because of its multiple leaf formation, shorter height than 'Candidum', and its very white interveins with dark green veins. 'Red Frill' was utilized because of its many bright red lance leaves and compact growth habit. Each of the parents of the novel cultivar is a commercial variety. The initial hybridization was made to produce a new caladium variety having improved leaf shape and color characteristics while retaining the desirable characteristics of the parent varieties such as compact growth and production of many leaves. This new and distinct cultivar, with its many brightly colored, wide lance leaves and large tubers, is suitable for forcing in containers, including hanging baskets, and can also be used as a landscape plant.

Caladiums are known for their diversity, with leaf colors ranging from white to dark red, color patterns varying from multicolored spots and blotches to solid colors, and leaf shapes from very elongated (strap), arrow-shaped (lance), or heart-shaped (fancy). Most of the lance leaf cultivars produce small, multi-segmented tubers which are not as profitable as the large tubers produced by fancy leaf cultivars, such as 'Candidum'. Rose colored caladiums which produce large tubes are missing among the commercially available lance leaf cultivars. 'Clarice', 'Lance Whorton', and 'Pink Gem' are offered in this color category, but they are multicolored rose and white and produce small tubers.

The most distinctive feature of the new variety is its production of rose colored, lance-leaved plants in combination with the production of relatively large tubers. The new variety has been named the 'Florida Sweetheart' cultivar.

Asexual reproduction of the new caladium variety, as performed in Bradenton, Fla., shows that the described characteristics and distinctions come true to form and are established and transmitted through secondary propagation. 'Florida Sweetheart' was vegetatively propagated using the commercial technique of "Chipping," whereby the mother tubers are divided into cubes measuring 0.75 to 1.0 inches on each side, with at least one surface containing axillary buds which develop into leaves. No obvious mutations have been observed in the field or greenhouse when this technique has been used with 'Florida Sweetheart'.

BRIEF DESCRIPTION OF THE DRAWING

The accompanying drawing is a photograph which shows typical specimens of the vegetative growth of the new variety and as depicted in color as nearly true as is reasonably possible in a color photograph of this nature.

DETAILED DESCRIPTION OF THE NEW VARIETY

Figure 1:
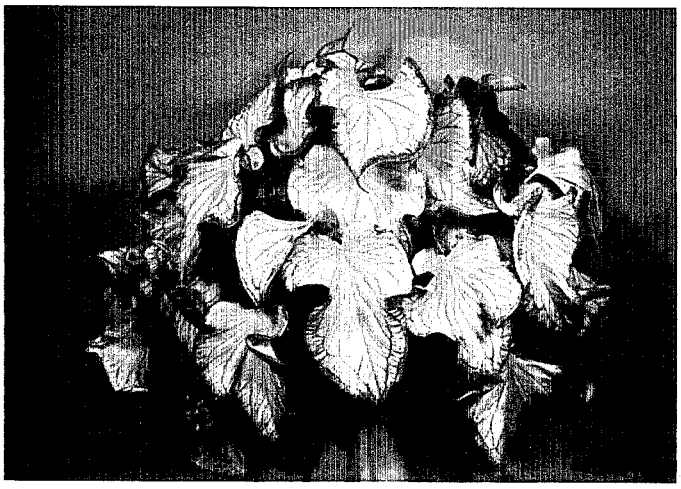

The following is a detailed description of the new variety with color terminology in accordance with British Color Council and The Royal Horticultural Society, *Horticultural Colour Chart*, except where general color terms of ordinary dictionary significance are obvious. Wherein dimensions, sizes, and other characteristics are given, it is to be understood that such characteristics are approximations of averages set forth as accurately as practicable. The description herein is from specimens grown in Bradenton, Fla., in 1986–1988.

Name: Florida Sweetheart.

Plant:

*Size.*—Up to a maximum 45 cm high after 3 months.

*Maturity.*—10.7 days (spring) to 18.5 days (summer) to first leaf unfurling, 26.3 days to market.

*Quality value.*—4.5–4.8 (scale of 1 to 5; 1=poor and 5=excellent).

Leaves:

*Number.*—Usually 35 to 40 produced by large tubers (>5 cm in diameter) grown in full sun and sandy soil; up to 43 leaves on some plants.

*Size.*—Up to 28 cm long and 18 cm wide.

*Shape.*—Peltate, sagittate-lanceolate, and have peniform venation.

*Color.*—Medium green (R.H.S. Green 143A) margins up to 2 cm wide, when grown in full sun. Interveinal areas are pale white (R.H.S. Yellow 40). When grown under 40–50% light occlusion, interveinal areas are light rose (R.H.S. red 54D) and are translucent, making main venation quite prominent. The color of the underside of the leaves is substantially the same as that of the top side of the leaves.

*Veinage.*—16 large veins radiating from central main vein, all of which are dark rose color (R.H.S. Red 51A). These connect marginally with a thin peripheral vein of lighter rose color (R.H.S. Red 54B) which parallels the leaf margin. A smaller, green (R.H.S. Green 143B) vein is located between, and parallels, the leaf margin peripheral lighter rose vein. Secondary rose veins are also a lighter rose color (R.H.S. 54B). Vein coloration on the underside of the leaves is a slightly dustier rose color (R.H.S. red 55B).

Tubers:

*Size.*—Produces tubers of various size ranging from "No. 2" to "Super Mammoth." The size grades are determined by measuring maximum diameter and are defined as follows: No. 2: ≧2.5 cm to <3.8 cm; No. 1: ≧3.8 cm to <6.4 cm; Jumbo: ≧6.4 cm to <8.9 cm; Mammoth: ≧8.9 cm to 11.4 cm; Super Mammoth: ≧11.4 cm.

*Shape.*—Multisegmented and have 8–10 dominant buds.

*Color.*—Light brown (R.H.S. Greyed Orange 164B) surface; light yellow (R.H.S. Yellow 11C) cortical area; dark brown (R.H.S. Greyed Orange 164A) leaf sheaths surrounding the dominant growth.

Production value index.—Range from 94.5 to 117.5. Production value index is defined as: N(No. 2)+2N (No. 1)+4N(Jumbo)+8N(Mammoth)+12N)(Super Mammoth); wherein N=number of tubers in each grade.

Inflorescence:

Up to 33 cm tall, with a simple spadix subtended by a herbaceous spathe; monoecious; spathe cuspidate up to 15.5 cm long and 2.4 cm wide with the upper ⅔ abaxial surface yellow white (R.H.S. 158B) and the adaxial surface slightly white (R.H.S. 158C), with the lower ⅓ abaxial surface yellow green (R.H.S. 145C) and the adaxial surface darker green (R.H.S. 145B); spadix up to 8 cm long, with the apical 4.6 cm consisting of yellow green stamens (R.H.S. 154D), and the basal 1.6 cm containing the yellow green pistils (R.H.S. 154D), with a central sterile yellow white area (R.H.S. 158B) of 1.2 cm; peduncle is elongated, round, up to 18.5 cm long, greyed-orange (R.H.S. 173D) with darker orange (R.H.S. 173C) longitudinal stripes up to 1.2 mm wide; stigma receptive approximately 3 days prior to pollen dehiscence; pistils and stamens are fertile. Fruit is yellow green (R.H.S. 154D) berry with 5–10 seeds. Between 40 and 70 berries develop per inflorescence.

Petioles:

Elongated, round, up to 20 cm long, color is a rose-brown (R.H.S. Greyed Red 182D) with darker brown specks (R.H.S. 177D). Petioles hold the young foliage upright, but tend to cascade when the leaves enlarge.

Total tuber weight of 'Florida Sweetheart' in 1986 was less than the fancy leaf cultivars 'Candidum' and 'Pink Beauty' but greater than 'Candidum Junior' and the lance leaf cultivars 'Red Frill' and 'Pink Gem'. All of the fancy leaf cultivars produced greater tuber mass than 'Florida Sweetheart', but the latter yielded more than 'Pink Gem'. When the number of marketable tubers was determined, 'Florida Sweetheart' was similar to 'Candidum', 'Pink Beauty', and 'Candidum Junior'. It produced a total number of tubers similar to 'Pink Gem', but a greater number of marketable tubers. The production value index, determined by number of tubers in each grade, was higher for 'Candidum', but 'Florida Sweetheart' yielded an index similar to 'Pink Beauty'. The distribution of tubers by grade in 1986 and 1987 showed that 'Florida Sweetheart' produces few (3.7–5.7%) mammoth tubers compared to the 12.3–22.7% mammoth and super mammoth tubers yielded by 'Candidum'. Over 70% of the tubers produced by 'Florida Sweetheart' were No. 1 or larger, compared to 47–52% for 'Pink Gem'. This size variation reflects the differences in marketable tubers and the production index comparisons between these two cultivars.

In the cultivars grown in 1988, tuber production of 'Florida Sweetheart' was less than 'Florida Roselight' and 'Pink Beauty', greater than 'Candidum Junior', 'Pink Gem', and 'Rosalie', and similar to the other cultivars. Numbers of marketable tubers were similar among 'Florida Sweetheart' and all other cultivars except 'Rosalie' and 'White Queen', which produced fewer. Production indices for 'Florida Roselight' and 'Pink Beauty' were greater than those of 'Florida Sweetheart', but the latter was similar to or greater than the remaining seven cultivars.

Forcing of tubers of 'Florida Sweetheart' was compared with both fancy- and lance-leaved cultivars since leaf shape is intermediate between the two. When grown in the spring of 1987 as three intact No. 1 tubers (>3<6.4 cm diameter) per 15 cm container in a glasshouse with 40% light exclusion, 'Florida Sweetheart' developed its first leaf as early as 'Pink Gem' and earlier than 'Candidum' and 'Candidum Junior'. Growth habit of the two lance leaf cultivars was similar and both were shorter, produced more leaves, and had a higher quality value than the fancy leaf types. During the summer of 1987, leaf development was quicker with 'Pink Gem' than with 'Florida Sweetheart', but plant heights were similar. 'Pink Gem' produced more leaves, but its fading color due to the higher temperatures and light intensities resulted in a lower quality index than 'Florida Sweetheart'. 'Florida Sweetheart' was compared to a number of cultivars grown in pots in the same glass house and showed that the lance leaf cultivars were shorter and produced more leaves than the fancy-leaved cultivars. This full, compact growth habit contributed to the higher quality indices received by these two cultivars.

In 1988, when grown in a black polypropylene shade house (25% light exclusion), the number of leaves was significantly increased for the 'Florida Sweetheart' and for most cultivars (nearly 100%) when the terminal buds were excised. 'Pink Gem' produced more leaves than 'Florida Sweetheart', but they were much smaller and the color was not as intense.

'Florida Sweetheart' is intended for forcing in containers of 10 to 25 cm in diameter but can be grown in sunny or shady locations in the landscape. Due to the cascading habit of the mature foliage, it makes an excellent hanging basket. Tubers should not be de-eyed when used in the large containers, because this produces many small leaves which are darker rose in color. Best foliage color is obtained when plants are grown with 40% light exclusion. Extensive research and evaluations have shown that this cultivar can be grown in either muck or sandy soils. Standard postharvest treatment of tubers is recommended and preplant hot water treatment of the tubers is encouraged to prolong the life of the stock.

The data provided hereinabove were published by the Florida Agricultural Experiment Station, Institute of Food and Agricultural Sciences (IAS) at the University of Florida, Gainesville, Fla., as Circular S-380.

I claim:

1. A new and distinct variety of caladium, substantially as illustrated and described, characterized by its wide lance leaves, rose colored leaf, and production of large tubers.

* * * * *

UNITED STATES PATENT AND TRADEMARK OFFICE

CERTIFICATE OF CORRECTION

PATENT NO. : PP 8,526

DATED : December 28, 1993

INVENTOR(S) : Gary J. Wilfret

It is certified that error appears in the above-identified patent and that said Letters Patent is hereby corrected as shown below:

Column 1, line 8: Delete "parents in unknown" should read --parents is unknown--.

Column 2, line 36: After "leaf unfurling" delete "," and insert --;--.

Column 6, line 5: Delete "(IAS)" and insert --(IFAS)--.

Signed and Sealed this

Seventeenth Day of May, 1994

*Attest:*

Bruce Lehman

BRUCE LEHMAN

*Attesting Officer*

*Commissioner of Patents and Trademarks*